United States Patent
Robinson et al.

(10) Patent No.: US 9,504,696 B2
(45) Date of Patent: *Nov. 29, 2016

(54) INTRACAMERAL SUSTAINED RELEASE THERAPEUTIC AGENT IMPLANTS

(71) Applicant: ALLERGAN, INC., Irvine, CA (US)

(72) Inventors: Michael R. Robinson, Irvine, CA (US); James A. Burke, Santa Ana, CA (US); Rhett M. Schiffman, Laguna Beach, CA (US); Alazar N. Ghebremeskel, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/746,438

(22) Filed: Jun. 22, 2015

(65) Prior Publication Data

US 2015/0283150 A1 Oct. 8, 2015

Related U.S. Application Data

(62) Division of application No. 14/031,657, filed on Sep. 19, 2013, now Pat. No. 9,061,065, which is a division of application No. 13/011,467, filed on Jan. 21, 2011, now Pat. No. 8,647,659.

(60) Provisional application No. 61/297,660, filed on Jan. 22, 2010.

(51) Int. Cl.
*A61K 9/58* (2006.01)
*A61K 31/5575* (2006.01)
(Continued)

(52) U.S. Cl.
CPC ......... *A61K 31/5575* (2013.01); *A61K 9/0024* (2013.01); *A61K 9/0051* (2013.01);
(Continued)

(58) Field of Classification Search
CPC .. A61K 9/0024; A61K 9/1647; A61L 27/18; A61L 27/54; A61L 27/58
See application file for complete search history.

(56) References Cited

U.S. PATENT DOCUMENTS 3,749,776 A 7/1973 Eakins et al.
4,997,652 A 3/1991 Wong
(Continued)

FOREIGN PATENT DOCUMENTS

WO 99-05263 2/1999
WO 02-02076 1/2002
(Continued)

OTHER PUBLICATIONS

Heller, Jorge, Biodegradable Polymers in Controlled Drug Delivery, Critical Reviews in Therapeutic Drug Carrier Systems, 1987, 39-90, 1 (1).

(Continued)

*Primary Examiner* — Carlos Azpuru
(74) *Attorney, Agent, or Firm* — Laura L. Wine; Debra D. Condino

(57) ABSTRACT

Described herein are intracameral implants including at least one therapeutic agent for treatment of at least one ocular condition. The implants described herein are not anchored to the ocular tissue, but rather are held in place by currents and gravity present in the anterior chamber of an eye. The implants are preferably polymeric, biodegradable and provide sustained release of at least one therapeutic agent to both the trabecular meshwork and associated ocular tissue and the fluids within the anterior chamber of an eye.

14 Claims, 5 Drawing Sheets

(51) Int. Cl.
| | |
|---|---|
| *A61K 9/00* | (2006.01) |
| *A61K 9/16* | (2006.01) |
| *A61L 27/18* | (2006.01) |
| *A61L 27/54* | (2006.01) |
| *A61L 27/58* | (2006.01) |
| *A61K 47/10* | (2006.01) |
| *A61K 47/34* | (2006.01) |

(52) U.S. Cl.
CPC ............ *A61K9/1647* (2013.01); *A61K 47/10* (2013.01); *A61K 47/34* (2013.01); *A61L 27/18* (2013.01); *A61L 27/54* (2013.01); *A61L 27/58* (2013.01)

(56) References Cited

U.S. PATENT DOCUMENTS

| | | | |
|---|---|---|---|
| 5,164,188 | A | 11/1992 | Wong |
| 5,166,331 | A | 11/1992 | Della Valle |
| 5,516,522 | A | 5/1996 | Peyman et al. |
| 5,716,981 | A | 2/1998 | Hunter et al. |
| 5,869,079 | A | 2/1999 | Wong et al. |
| 5,965,152 | A | 10/1999 | Galin et al. |
| 5,972,326 | A | 10/1999 | Galin et al. |
| 6,309,669 | B1 | 10/2001 | Setterstrom et al. |
| 6,369,116 | B1 | 4/2002 | Wong et al. |
| 7,589,057 | B2 | 9/2009 | Chang et al. |
| 7,799,326 | B2 * | 9/2010 | Bromme ............ A61K 38/4873 424/146.1 |
| 7,799,336 | B2 | 9/2010 | Hughes et al. |
| 7,993,634 | B2 | 8/2011 | Hughes |
| 8,206,736 | B2 | 6/2012 | Hughes |
| 8,206,737 | B2 | 6/2012 | Hughes |
| 8,409,607 | B2 * | 4/2013 | Hughes ................ A61K 9/0051 424/428 |
| 8,481,069 | B2 * | 7/2013 | Hughes ................ A61K 9/0051 424/428 |
| 8,637,068 | B2 * | 1/2014 | Hughes ................ A61K 9/0051 424/426 |
| 9,061,065 | B2 * | 6/2015 | Robinson ............ A61K 9/0051 |
| 2002/0032201 | A1 | 3/2002 | Olejnik |
| 2002/0035264 | A1 | 3/2002 | Kararli |
| 2002/0094998 | A1 | 7/2002 | Burke et al. |
| 2004/0151753 | A1 | 8/2004 | Chen et al. |
| 2005/0101582 | A1 | 5/2005 | Lyons |
| 2005/0181017 | A1 | 8/2005 | Hughes |
| 2005/0244464 | A1 | 11/2005 | Hughes |
| 2005/0244469 | A1 | 11/2005 | Whitcup et al. |
| 2006/0173060 | A1 | 8/2006 | Chang et al. |
| 2006/0182781 | A1 | 8/2006 | Hughes |
| 2006/0246145 | A1 | 11/2006 | Chang |
| 2007/0224246 | A1 | 9/2007 | Hughes et al. |
| 2007/0224278 | A1 | 9/2007 | Lyons et al. |
| 2007/0293873 | A1 | 12/2007 | Chang |
| 2008/0033351 | A1 | 2/2008 | Trogden |
| 2008/0097335 | A1 | 4/2008 | Trogden et al. |
| 2008/0131481 | A1 | 6/2008 | Hughes |
| 2008/0131484 | A1 | 6/2008 | Robinson |
| 2008/0145403 | A1 * | 6/2008 | Spada ................ A61K 9/0051 424/426 |
| 2008/0292679 | A1 | 11/2008 | Lyons |
| 2009/0082321 | A1 | 3/2009 | Edelman et al. |
| 2009/0148527 | A1 | 6/2009 | Robinson et al. |
| 2009/0149435 | A1 | 6/2009 | Wang |
| 2010/0104654 | A1 | 4/2010 | Robinson et al. |
| 2010/0124565 | A1 | 5/2010 | Spada et al. |
| 2010/0185205 | A1 | 7/2010 | Novakovic et al. |
| 2010/0247606 | A1 | 9/2010 | Robinson |
| 2010/0278898 | A1 | 11/2010 | Hughes et al. |
| 2011/0152328 | A1 | 6/2011 | Whitcup |
| 2011/0182966 | A1 | 7/2011 | Robinson |
| 2011/0250285 | A1 | 10/2011 | Hughes |
| 2012/0219611 | A1 | 8/2012 | Hughes |
| 2012/0238633 | A1 | 9/2012 | Hughes |
| 2012/0276184 | A1 | 11/2012 | Ghebremeskel et al. |
| 2012/0276186 | A1 | 11/2012 | Ghebremeskel et al. |
| 2013/0071349 | A1 | 3/2013 | Robinson et al. |

FOREIGN PATENT DOCUMENTS

| | | |
|---|---|---|
| WO | 02-43785 | 6/2002 |
| WO | 03-024420 | 3/2003 |
| WO | 2009-143288 | 11/2009 |
| WO | 2012-149278 | 11/2012 |
| WO | 2012-149287 | 11/2012 |

OTHER PUBLICATIONS

Higginbotham, Eve, et al., One-Year, Randomized Study Comparing Bimatoprost and Timolol in Glaucoma and Ocular Hypertension, Archives of Ophthalmology, Oct. 2002, 1286-1293, 120 (10), US.

International Search Report dated Jan. 26, 2012, PCT/US2011/021971.

Janoria, Kumar, et al., Novel approaches to retinal drug delivery, Expert Opinion on Drug Delivery, Jul. 1, 2007, 376-377, 4.

Maruquis, Robert, et al., Management of Glaucoma: Focus on Pharmacological Therapy, Drugs & Aging, 2005, 1-21, 22 (1).

Moshfeghi, Darius, et al., Retinal and Choroidal Vascular Occlusion After Posterior Sub-Tenon Triamcinolone Injection, American Journal of Ophthalmology, 2002, 132-134, vol. 134.

Nordstrom, et al., Persistence and Adherence With Topical Glaucoma Therapy, American Journal of Ophthalmology, 2005, 598-608, 140, US.

Seah, Steve, et al., Use of Surodex in Phacotrabeculectomy Surgery, Am J Ophthalmol, May 2005, 927-928, 139(5).

Stewart, William, et al., The Efficacy and Safety of Latanoprost 0.005% Once Daily Versus Brimonidine 0.2% Twice Daily in Open-Angle Glaucoma or Ocular Hypertension, Am J Ophthalmol, May 2001, 631-635, 131.

Tan, Donald, et al., Randomized Clinical Trial of a New Dexamethasone Delivery System (Surodex) for Treatment of Post-Cataract Surgery Inflammation, Ophthalmology, Feb. 1999, 223-231, 106 (2).

Tan, Donald, et al., Randomized Clinical Trial of Surodex Steroid Drug Delivery System for Cataract Surgery: Anterior Versus Posterior Placement of Two Surodex in the Eye, Ophthalmology, Dec. 2001, 2172-2181, 108(12).

U.S. Appl. No. 11/368,845, filed Mar. 6, 2006.
U.S. Appl. No. 11/371,118, filed Mar. 8, 2006.
U.S. Appl. No. 12/761,765, filed Apr. 16, 2010.
U.S. Appl. No. 13/152,780, filed Jun. 3, 2011.
U.S. Appl. No. 13/466,752, filed May 8, 2012.
U.S. Appl. No. 13/466,804, filed May 8, 2012.

United States Board of Appeals and Interferences decision on appeal in Ex parte Huang et al, Appeal No. 2009-013914, U.S. Appl. No. 10/340,237, mailed Sep. 21, 2010.

United States Board of Patent and Interferences decision on appeal in Ex parte Huang et al, Appeal No. 2010-006865, U.S. Appl. No. 10/836,880, mailed Sep. 28, 2010.

United States Board of Patent Appeals and Interferences decision on appeal in Ex parte Hughes et al, Appeal No. 2010-004999, U.S. Appl. No. 10/836,911, mailed Oct. 25, 2010.

United States Board of Patent Appeals and Interferences on appeal in Ex parte Hughes et al, Appeal No. 2011-003859, U.S. Appl. No. 11/116,698, mailed Aug. 1, 2011.

United States Pharmacopeia, The National Formulary, USP23, 1995, 1790-1798, 18.

Wadood, Azfar, et al., Safety and Efficacy of a Dexamethasone Anterior Segment Delivery System in Patients After Phacoemulsification, Journal of Cataract and Refractive Surgery, Apr. 2004, 761-768, 30.

Woodward, et al., "Fixed-Combination and Emerging Glaucoma Therapies", Expert Opinion on Emerging Drugs, 2007, 313-327, 12 (2).

* cited by examiner

Implant

INTRACAMERAL SUSTAINED RELEASE THERAPEUTIC AGENT IMPLANTS

CROSS-REFERENCE

This application is a divisional of copending U.S. application Ser. No. 14/031,657, filed on Sep. 19, 2013, which is a divisional of U.S. application Ser. No. 13/011,467, filed on Jan. 21, 2011, now issued as U.S. Pat. No. 8,647,659, which claims the benefit of U.S. Provisional Patent Application Ser. No. 61/297,660, filed on Jan. 22, 2010, the entire disclosure of which is incorporated herein by this specific reference. The entire disclosure of the aforementioned patent applications are incorporated herein by reference.

FIELD OF THE INVENTION

The present invention relates to intracameral sustained release implants and methods of making and using the same.

SUMMARY

Described herein are intraocular systems and methods for treating ocular conditions. In particular, local administration of a sustained release therapeutic agent delivery system to the anterior chamber and/or to anterior vitreous chamber of the eye to treat aqueous chamber elevated intraocular pressure is described.

Further, described herein are methods for treating an ocular condition comprising the steps of: providing at least two biodegradable sustained release implants containing at least one therapeutic agent; implanting the at least two biodegradable sustained release implants into the anterior chamber of an eye; and treating the ocular condition, wherein the at least two biodegradable sustained release implants release about 100 ng per day of the at least one bioactive agent for a period greater than about 1 month.

Further still, described herein are methods for treating glaucoma in an eye comprising the steps of: providing at least two biodegradable sustained release implants containing at least one therapeutic agent; implanting the at least two biodegradable sustained release implants into the anterior chamber of the eye; allowing a sufficient time for the at least two biodegradable sustained release implants to settled out in the inferior angle; allowing a sufficient time for the at least two biodegradable sustained release implants to release the at least one therapeutic agent; and treating glaucoma, wherein the at least two biodegradable sustained release implants release about 100 ng per day of the at least one bioactive agent for a period greater than about 1 month.

In one embodiment, the ocular condition is glaucoma and/or elevated intraocular pressure. The sustained release implants can release about 70% of the at least one therapeutic agent over the first month. In some embodiments, the at least one therapeutic agent can comprise about 30% of the at least two biodegradable sustained release implants and is selected from the group consisting of latanoprost, bimatoprost and travoprost and their salts, esters and prodrugs.

In another embodiment, the at least two biodegradable sustained release implants comprise about 5% to about 70% poly(D,L-lactide). In other embodiments, the at least two biodegradable sustained release implants comprise about 5% to about 40% poly(D,L-lactide-co-glycolide). In yet other embodiments, the at least two biodegradable sustained release implants comprise about 5% to about 40% polyethylene glycol.

In still other example embodiments, the at least two biodegradable sustained release implants comprise about 30% therapeutic agent, 65% poly(D,L-lactide), and 5% polyethylene glycol or about 20% therapeutic agent, 55% poly(D,L-lactide), 10% poly(D,L-lactide-co-glycolide), and 5% polyethylene glycol.

The implants themselves can be inserted into the ocular tissue using an appropriate applicator. Once implanted, the at least two biodegradable sustained release implants can settle out in the inferior angle within 24 hours of implanting within the anterior chamber.

In one embodiment, the sufficient time for the at least two biodegradable sustained release implants to release the at least one therapeutic agent is greater than about 42 days.

DEFINITION OF TERMS

Figure 1:
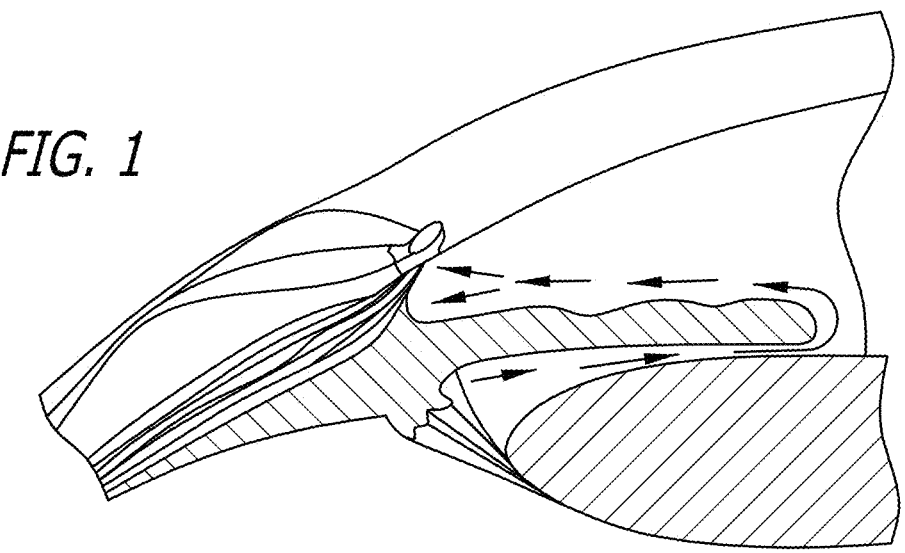
FIG. 1 illustrates the two different pathways for aqueous humor outflow from the anterior chamber both located in the iridocorneal angle.

"About" means plus or minus ten percent of the number, parameter or characteristic so qualified.

"Biodegradable polymer" means a polymer or polymers which degrade in vivo, and wherein erosion of the polymer or polymers over time occurs concurrent with or subsequent to release of the therapeutic agent. The terms "biodegradable" and "bioerodible" are used interchangeably herein. A biodegradable polymer may be a homopolymer, a copolymer, or a polymer comprising more than two different polymeric units. The polymer can be a gel or hydrogel type polymer, polylactic acid or poly(lactic-co-glycolic) acid or polyethylene glycol polymer or mixtures or derivatives thereof.

"Ocular condition" means a disease, ailment or condition which affects or involves the ocular region. Broadly speaking, the eye includes the eyeball and the tissues and fluids which constitute the eyeball, the periocular muscles (such as the oblique and rectus muscles) and the portion of the optic nerve which is within or adjacent to the eyeball.

An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the retina but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic ophthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

"Ocular region" or "ocular site" means any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include the anterior (aqueous) chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically-induced avascular regions, the macula, and the retina.

"Sustained release" or "controlled release" refers to the release of at least one therapeutic bioactive agent, or drug, from an implant at a predetermined rate. Sustained release implies that the therapeutic bioactive agent is not released from the implant sporadically in an unpredictable fashion and does not "burst" from the implant upon contact with a biological environment (also referred to herein as first order kinetics) unless specifically intended to do so. However, the term "sustained release" as used herein does not preclude a "burst phenomenon" associated with deployment. In some example embodiments according to the present description an initial burst of at least one therapeutic agent may be desirable followed by a more gradual release thereafter. The release rate may be steady state (commonly referred to as "timed release" or zero order kinetics), that is the at least one therapeutic agent is released in even amounts over a predetermined time (with or without an initial burst phase) or may be a gradient release. For example, sustained release can have substantially no fluctuations in therapeutic agent delivery as compared to topical administration.

"Therapeutically effective amount" means level or amount of agent needed to treat an ocular condition, or reduce or prevent ocular injury or damage without causing significant negative or adverse side effects to the eye or a region of the eye. In view of the above, a therapeutically effective amount of a therapeutic agent, such as a latanoprost, is an amount that is effective in reducing at least one symptom of an ocular condition.

DETAILED DESCRIPTION

Described herein are intracameral implants including at least one therapeutic agent. The implants described herein are placed in the anterior chamber of an eye, but are not anchored to the ocular tissue. Rather, the implants are held in place by currents and gravity present in the anterior chamber of the eye. The implants are preferably polymeric, biodegradable and provide sustained release of at least one therapeutic agent to both the trabecular meshwork (TM) and associated ocular tissues, and the fluids within the anterior chamber of the implanted eye.

Direct intracameral or anterior intravitreal administration of sustained release implants or therapeutic agent delivery systems, as set forth herein, are effective in treating an array of ocular conditions outlined herein. On such condition is glaucoma characterized by elevated intraocular pressure which can be treated as described herein by bypassing the robust scleral drug clearance mechanisms (e.g. topical drops).

Intraocular pressure (IOP) variation appears to be an independent risk factor for glaucomatous damage. Conventional therapy for treating ocular hypertension or glaucoma is the use of anti-hypertensive topical ophthalmic drops to lower the IOP. Unfortunately, bolus dosing with topical ophthalmic drops results in anterior chamber therapeutic agent levels with peak and trough levels that results in variability of IOP control over time. This fluctuation in IOP can result in glaucomatous field progression, especially in patients with advanced glaucoma. Addressing this unmet need in patients with ocular hypertension or glaucoma that require medical therapy, are the sustained-release intracameral implants described herein. The implants can establish low fluctuations of the IOP throughout the day and the night when topical drops are inconvenient. A nocturnal IOP spike occurs between 11 pm and 6 am in patients with open angle glaucoma, and this may contribute to progressive visual field loss in some patients. The additional limitation of topical therapy is the lack of steady state drug concentrations in the anterior chamber with bolus dosing not controlling nocturnal IOP elevations in a number of patients. The implants described herein establish low fluctuations of the IOP throughout the night as well, thereby alleviating the complications of topical administration in the nighttime hours.

Non-compliance with a medical regimen containing one or more topical eye drops to treat ocular hypertension or glaucoma occurs in over 50% of patients and this may contribute to Iop fluctuation during the day when drops are not used on a regular schedule. The implants described herein do not require such compliance, and are therefore more patient friendly.

Described herein are intracameral sustained release therapeutic agent implants that provide continuous release of the therapeutic agent thereby avoiding the peak and trough therapeutic agent levels that occur in the aqueous humor with topical dosing. The steady state drug concentrations achieved in the aqueous humor with the implants described herein can significantly lower the IOP fluctuation during the day and night unlike conventional topical administration of drugs.

The anterior and posterior chambers of the eye are filled with aqueous humor, a fluid predominantly secreted by the ciliary body with an ionic composition similar to the blood. The function of the aqueous humor is two-fold: 1) to supply nutrients to the avascular structures of the eye, such as the lens and cornea, 2) maintain IOP within its physiological range. Maintenance of IOP and supply of nutrients to the anterior segment are factors that are critical for maintaining normal visual acuity.

Figure 2:
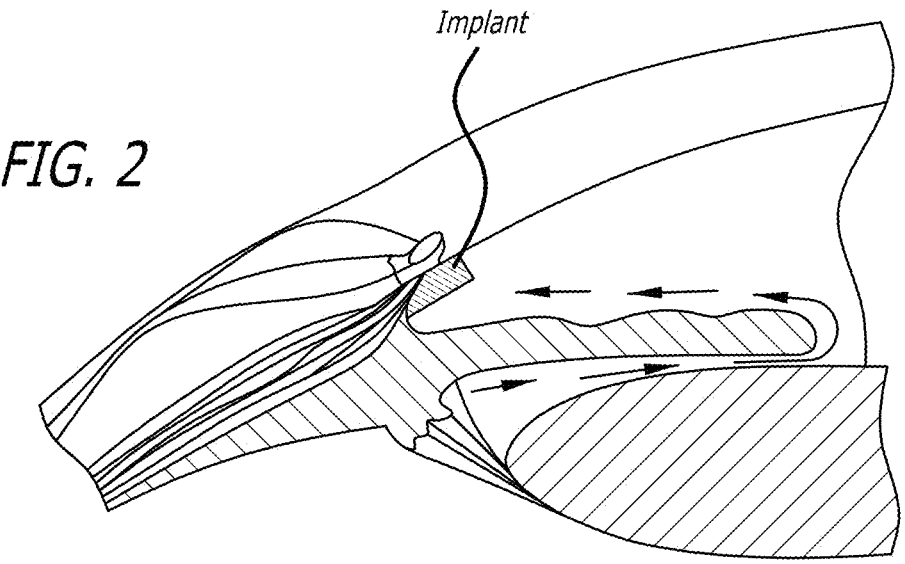
FIG. 2 illustrates the placement of an implant as described herein at the location of aqueous humor outflow from the anterior chamber.

Aqueous humor is predominantly secreted to the posterior chamber of the eye by the ciliary processes of the ciliary body and a minor mechanism of aqueous humor production is through ultrafiltration from arterial blood (FIG. 1). Aqueous humor then reaches the anterior chamber by crossing the pupil and there are convection currents where the flow of aqueous adjacent to the iris is upwards, and the flow of aqueous adjacent to the cornea flows downwards (FIG. 2).

There are two different pathways of aqueous humor outflow, both located in the iridocorneal angle of the eye (FIG. 1). The uveoscleral or nonconventional pathway refers to the aqueous humor leaving the anterior chamber by diffusion through intercellular spaces among ciliary muscle fibers. Although this seems to be a minority outflow pathway in humans, the uveoscleral or nonconventional pathway is the target of specific anti-hypertensive drugs such as the hypotensive lipids that increase the functionality of this route through remodeling of the extracellular matrix.

Figure 3:
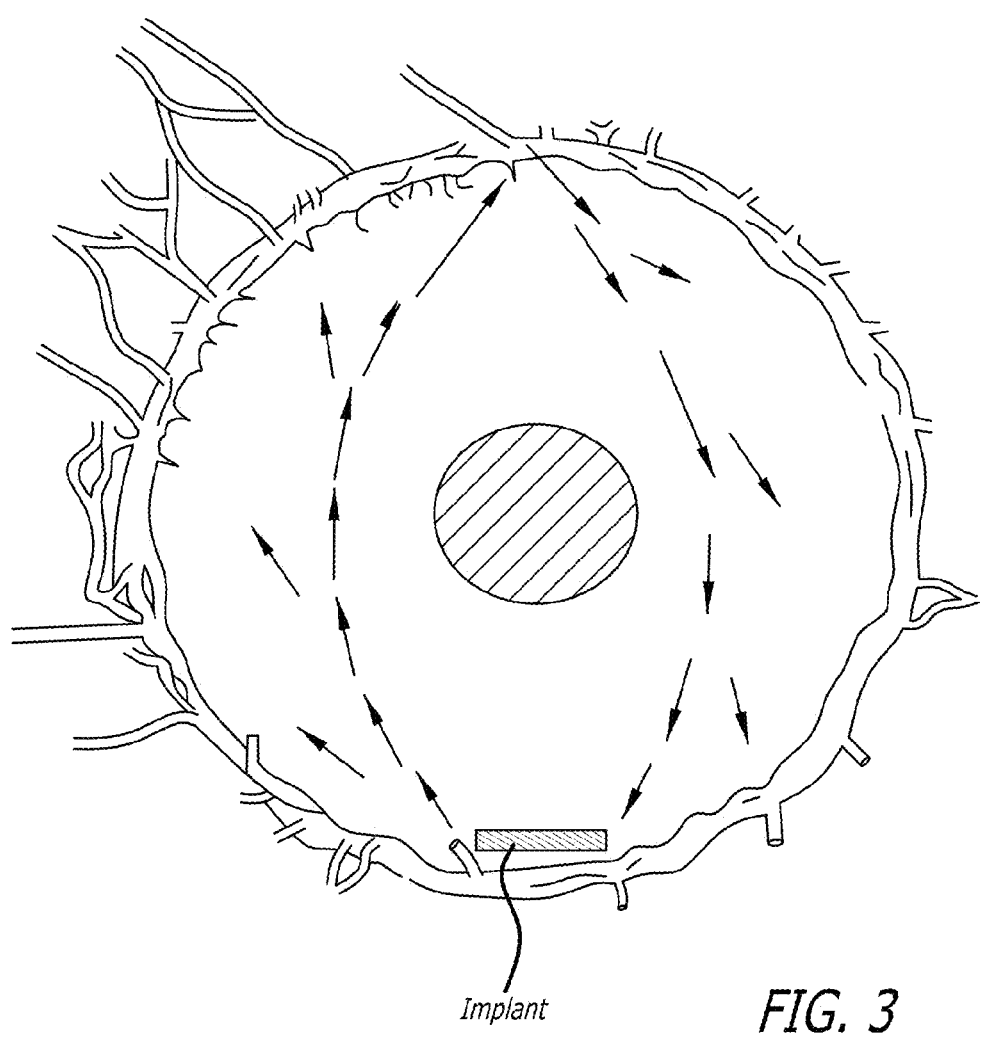
FIG. 3 illustrates the currents located within the anterior chamber of an eye as well as a possible location of an implant or implants as described herein.

The aqueous humor drains 360 degrees into the trabecular meshwork that initially has pore size diameters ranging from 10 to under 30 microns in humans. Aqueous humor drains through Schlemm's canal and exits the eye through 25 to 30 collector channels into the aqueous veins, and eventually into the episcleral vasculature and veins of the orbit (see FIG. 3). FIG. 3 is a schematic drawing in which the arrows indicate aqueous humor convection currents in the anterior chamber of an eye. An implant as described herein releasing at least one therapeutic agent is shown placed inferiorly. Free therapeutic agents eluting from the implant enters the aqueous humor convection currents (arrows). The therapeutic agents are then dispersed throughout the anterior chamber and enter the target tissues such as the trabecular meshwork and the ciliary body region through the iris root region.

An advantage of intracameral injection and placement of the biodegradable implant described herein is that the anterior chamber is an immune privileged site in the body and less likely to react to foreign material, such as polymeric therapeutic agent delivery systems. This is not the case in the sub-Tenon's space where inflammatory reactions to foreign materials are common. In addition to the anterior chamber containing immunoregulatory factors that confer immune privilege, particles with diameters greater than 30 microns are less immunogenic and have a lower propensity toward causing ocular inflammation. Resident macrophages in the eye are the first line of defense with foreign bodies or infectious agents; however, particles larger than 30 microns are difficult to phagocytose. Therefore, particles larger than 30 microns are less prone to macrophage activation and the inflammatory cascade that follows. This reduction in inflammation response is beneficial to a patient.

The efficiency of delivering therapeutic agents or drugs to the aqueous humor with a polymeric release system is much greater with an intracameral location when compared to a sub-Tenon application. Thus, less than 1% of therapeutic agent delivered in the sub-Tenon's space will enter the aqueous humor whereas 100% of the drug released intracamerally will enter the aqueous humor. Therefore, lower therapeutic agent loads are required for the intracameral drug delivery systems described herein compared to sub-Tenon's applications.

As such, there will be less exposure of the conjunctiva to therapeutic agents, and as a result, less propensity toward developing conjunctival hyperemia when delivering topical therapeutic agents, such as prostaglandins and prostamides. Lastly, the therapeutic agent(s) will enter the conjunctival/episcleral blood vessel via the aqueous veins directly following intracameral implantation. This minimizes conjunctival hyperemia with, for example, prostaglandin analogues compared with a sub-Tenon's injection where numerous vessels are at risk of dilation with a high concentration of therapeutic agent present diffusely in the extravascular space of the conjunctiva. Direct intracameral implantation also obviates the need for preservatives, which when used in topical drops, can irritate the ocular surface.

The implants described herein are made of polymeric materials to provide maximal approximation of the implant to the iridocorneal angle. In addition, the size of the implant, which ranges from a diameter, width or cross-section of about 0.1 mm to about 1 mm, and lengths from about 0.1 mm to about 6 mm, enables the implant to be inserted into the anterior chamber using an applicator with a small gauge needle ranging from about 22 G to about 30 G.

The polymer materials used to form the implants described herein can be any combination of polylactic acid, glycolic acid, and/or polyethylene glycol that provides sustained-release of the therapeutic agent into the outflow system of the eye over time. Other polymer-based sustained release therapeutic agent delivery systems for hypotensive lipids can also be used intracamerally to reduce IOP.

The intracameral implants described herein can release therapeutic agent loads over various time periods. The implants, when inserted intracamerally or into the anterior vitreous, provide therapeutic levels of at least one therapeutic agent for extended periods of time. Extended periods of time can be about 1 week, about 6 weeks, about 6 months, about 1 year or longer.

Suitable polymeric materials or compositions for use in the implants include those materials which are compatible, that is biocompatible, with the eye so as to cause no substantial interference with the functioning or physiology of the eye. Such materials preferably are at least partially, and more preferably, substantially biodegradable or bioerodible.

In one embodiment, examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. non-oxo-carbonyl, such as carboxylic acid ester, and the like. The nitrogen may be present as amide, cyano and amino.

In one embodiment, polymers of hydroxyaliphatic carboxylic acids, either homopolymers or copolymers, and polysaccharides are useful in the implants. Polyesters can include polymers of D-lactic acid, L-lactic acid, racemic lactic acid, glycolic acid, polycaprolactone, and combinations thereof. Generally, by employing the L-lactate or D-lactate, a slowly eroding polymer or polymeric material is achieved, while erosion is substantially enhanced with the lactate racemate. Useful polysaccharides and polyethers can include, without limitation, polyethylene glycol (PEG), calcium alginate, and functionalized celluloses, particularly carboxymethylcellulose esters characterized by being water insoluble and having a molecular weight of about 5 kD to about 500 kD, for example.

Other polymers of interest include, without limitation, polyvinyl alcohol, polyesters, and combinations thereof which are biocompatible and may be biodegradable and/or bioerodible. Some preferred characteristics of the polymers or polymeric materials for use in the present implants may include biocompatibility, compatibility with the selected therapeutic agent, ease of use of the polymer in making the therapeutic agent delivery systems described herein, a desired half-life in the physiological environment, and water insolubility.

In one embodiment, an intracameral implant according to the present description has a formulation of 30% therapeutic agent, 45% R203S poly(D,L-lactide), 20% R202H poly(D,L-lactide), and 5% PEG 3350. In another embodiment, the formulation is 20% therapeutic agent, 45% R203S poly(D,L-lactide), 10% R202H poly(D,L-lactide), 20% RG752S poly(D,L-lactide-co-glycolide), and 5% PEG 3350. The range of concentrations of the constituents that can be used are about 5% to about 40% therapeutic agent, about 10% to about 60% R203S, about 5% to about 20% R202H, about 5% to about 40% RG752S, and 0 to about 15% PEG 3350. Specific polymers may be omitted, and other types added, to adjust the therapeutic agent release rates. The polymers used are commercially available.

The polymers used to form the implant have independent properties associated with them that when combined provide the properties needed for sustained release of at least one therapeutic agent once implanted. For example, R203S poly(D,L-lactide) has an inherent viscosity, or mean viscosity, of about 0.25 to about 0.35 dl/g whereas R202H poly(D,L-lactide) has a lower inherent viscosity of about 0.16 to about 0.24 dl/g. As such, the polymer compositions described herein can have a mixture of higher and lower molecular weight poly(D,L-lactide). Likewise, RG752S poly(D,L-lactide-co-glycolide) has a molar ratio of D,L-lactide:glycolide of about 73:27 to about 77:23 and an inherent viscosity of about 0.16 to about 0.24 dl/g. The polyethylene glycol used herein can have a molecular weight for example of about 3,000 to about 3,500 g/mol, preferably about 3,350 g/mol. Polymers having different inherent viscosities and/or molecular weights can be combined to arrive at a polymeric composition appropriate for sustained release of a particular therapeutic agent or agents.

The biodegradable polymeric materials which are included to form the implant's polymeric matrix are preferably subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Equally important to controlling the biodegradation of the polymer and hence the extended release profile of the implant is the relative average molecular weight of the polymeric composition employed in the implants. Different molecular weights of the same or different polymeric compositions may be included to modulate the release profile of the at least one therapeutic agent.

The implants described herein can be monolithic, i.e. having the at least one therapeutic agent homogenously distributed throughout the polymeric matrix, or encapsulated, where a reservoir of therapeutic agent is encapsulated by the polymeric matrix. In addition, the therapeutic agent may be distributed in a non-homogenous pattern in the matrix. For example, the implants may include a portion that has a greater concentration of the therapeutic agent relative to a second portion of the implant which may have less.

The total weight of an implant is dependent on the volume of the anterior chamber and the activity or solubility of the therapeutic agent. Often, the dose of therapeutic agent is generally about 0.1 mg to about 200 mg of implant per dose. For example, an implant may weigh about 1 mg, about 3 mg, about 5 mg, about 8 mg, about 10 mg, about 100 mg about 150 mg, about 175 mg, or about 200 mg, including the incorporated therapeutic agent.

A load of therapeutic agent associated with an implant will have a sustained release property or profile associated with it. For example, over the first 30 days after implantation, the implants described herein can release about 1 μg/day to about 20 μg/day. Over the lifetime of an implant, about 100 ng/day to about 900 ng/day can be released. In other embodiments, about 300 ng/day, about 675 ng/day or about 700 ng/day of therapeutic agent is released.

The proportions of the therapeutic agent, polymer and any other modifiers may be empirically determined by formulating several implant batches with varying average proportions. Release rates can be estimate, for example, using the infinite sink method, a weighed sample of the implants is added to a measured volume of a solution containing 0.9% NaCl in water, where the solution volume will be such that the therapeutic agent concentration after release is less than 5% of saturation. The mixture is maintained at 37° C. and stirred slowly. The appearance of the dissolved therapeutic agent as a function of time may be followed by various methods known in the art, such as spectrophotometrically, HPLC, mass spectroscopy, and the like until the absorbance becomes constant or until greater than 90% of the therapeutic agent has been released.

The therapeutic agents that can be used with the implants described herein are prostaglandins, prostaglandin analogues, and prostamides. Examples include prostaglandin receptor agonists including prostaglandin $E_1$ (alprostadil), prostaglandin $E_2$ (dinoprostone), latanoprost and travoprost. Latanoprost and travoprost are prostaglandin prodrugs (i.e. I-isopropyl esters of a prostaglandin); however, they are referred to as prostaglandins because they act on the prostaglandin F receptor, after being hydrolyzed to the 1-carboxylic acid. A prostamide (also called a prostaglandinethanolamide) is a prostaglandin analogue, which is pharmacologically unique from a prostaglandin (i.e. because prostamides act on a different cell receptor [the prostamide receptor] than do prostaglandins), and is a neutral lipid formed a as product of cyclo-oxygenase-2 ("COX-2") enzyme oxygenation of an endocannabinoid (such as anandamide). Additionally, prostamides do not hydrolyze in situ to the 1-carboxylic acid. Examples of prostamides are bimatoprost (the synthetically made ethyl amide of 17-phenyl prostaglandin $F_{2\alpha}$) and prostamide $F_{2\alpha}$. Other prostaglandin analogues that can be used as therapeutic agents include, but are not limited to, unoprostone, and $EP_2/EP_4$ receptor agonists.

Prostaglandins as used herein also include one or more types of prostaglandin derivatives, prostaglandin analogues including prostamides and prostamide derivatives, prodrugs, salts thereof, and mixtures thereof. In certain implants, the prostaglandin comprises a compound having the structure

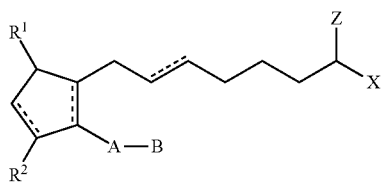

wherein the dashed bonds represent a single or double bond which can be in the cis or trans configuration; A is an alkylene or alkenylene radical having from two to six carbon atoms, which radical may be interrupted by one or more oxide radicals and substituted with one or more hydroxy, oxo, alkyloxy or alkylcarboxy groups wherein the alkyl radical comprises from one to six carbon atoms; B is a cycloalkyl radical having from three to seven carbon atoms, or an aryl radical, selected from hydrocarbyl aryl and heteroaryl radicals having from four to ten carbon atoms wherein the heteroatom is selected from nitrogen, oxygen and sulfur atoms; X is $—OR^4$ or $—N(R^4)_2$ wherein $R^4$ is selected from hydrogen, a lower alkyl radical having from one to six carbon atoms,

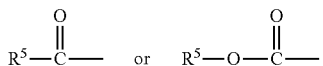

wherein $R^5$ is a lower alkyl radical having from one to six carbon atoms; Z is =O or represents two hydrogen radicals; one of $R^1$ and $R^2$ is =O, —OH or a —O(CO)$R^6$ group, and the other one is —OH or —O(CO)$R^6$, or $R^1$ is =O and $R^2$ is hydrogen, wherein $R^6$ is a saturated or unsaturated acyclic hydrocarbon group having from 1 to about 20 carbon atoms, or —(CH2)$_m R^7$ wherein m is 0 or an integer of from 1 to 10, and $R^7$ is cycloalkyl radical, having from three to seven carbon atoms, or a hydrocarbyl aryl or heteroaryl radical, as defined above, or a pharmaceutically-acceptable salt thereof.

Pharmaceutically acceptable acid addition salts of the compounds described are those formed from acids which form non-toxic addition salts containing pharmaceutically acceptable anions, such as the hydrochloride, hydrobromide, hydroiodide, sulfate, or bisulfate, phosphate or acid phosphate, acetate, maleate, fumarate, oxalate, lactate, tartrate, citrate, gluconate, saccharate and p-toluene sulphonate salts.

In one example embodiment, the implants include a prostaglandin having the structure

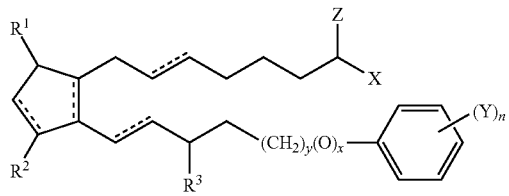

wherein y is 0 or 1, x is 0 or 1 and x and y are not both 1, Y is selected the group consisting of alkyl, halo, nitro, amino, thiol, hydroxy, alkyloxy, alkylcarboxy and halo substituted alkyl, wherein said alkyl radical comprises from one to six carbon atoms, n is 0 or an integer of from 1 to 3 and $R^3$ is =O, —OH or O(CO)$R^6$.

In additional example embodiments, the prostaglandin has the formula

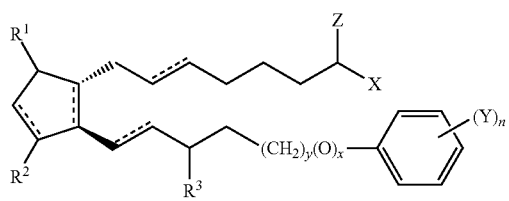

wherein hatched lines indicate the alpha configuration and solid triangles indicate the beta configuration.

In some implants described herein, the prostaglandin has the formula

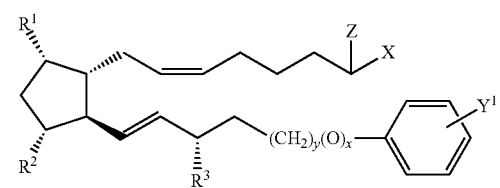

wherein $Y^1$ is CI or trifluoromethyl.

Other prostaglandins can have the following formula

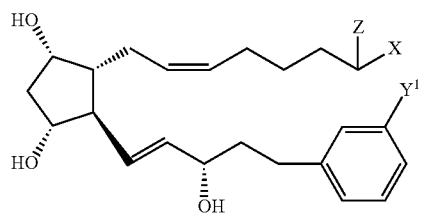

and 9-, 11- and/or 15 esters thereof.

In one example embodiment, the prostaglandin component comprises a compound having the formula

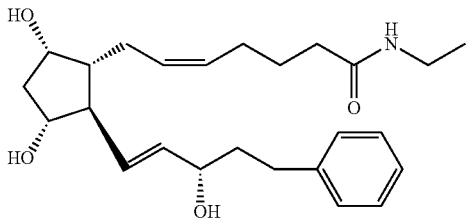 [SMILES: CCNC(=O)CCC/C=C\C[C@@H]1[C@@H](/C=C/[C@@H](O)CCc2ccccc2)[C@H](O)C[C@@H]1O]

This compound is also known as bimatoprost and is publicly available in a topical ophthalmic solution under the tradename, LUMIGAN® (Allergan, Inc., Irvine, Calif.).

In another example embodiment of an intraocular implant, the prostaglandin comprises a compound having the structure

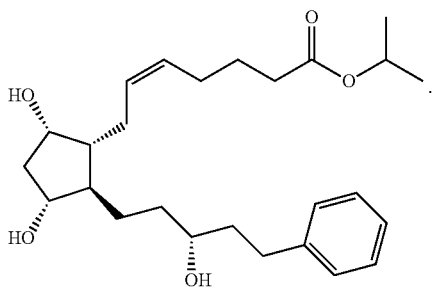 [SMILES: CC(C)OC(=O)CCC/C=C\C[C@@H]1[C@@H](CC[C@@H](O)CCc2ccccc2)[C@H](O)C[C@@H]1O]

This prostaglandin is known as latanoprost and is publicly available in a topical ophthalmic solution under the tradename, XALATAN®. Thus, the implants may comprise at least one therapeutic bioactive agent which comprises, consists essentially of, or consists of latanoprost, a salt thereof, isomer, prodrug or mixtures thereof.

The prostaglandin component may be in a particulate or powder form and it may be entrapped by the biodegradable polymer matrix. Usually, prostaglandin particles will have an effective average size less than about 3000 nanometers. In certain implants, the particles may have an effective average particle size about an order of magnitude smaller than 3000 nanometers. For example, the particles may have an effective average particle size of less than about 500 nanometers. In additional implants, the particles may have an effective average particle size of less than about 400 nanometers, and in still further embodiments, a size less than about 200 nanometers.

Other therapeutic agents useful with the intracameral implants described herein, include, but are not limited to beta-adrenergic receptor antagonists (such as timolol, betaxolol, levobetaxolol, carteolol, levobunolol, and propranolol, which decrease aqueous humor production by the ciliary body); alpha adrenergic receptor agonists such as brimonidine and apraclonidine (iopidine) (which act by a dual mechanism, decreasing aqueous production and increasing uveoscleral outflow); less-selective sympathomimetics such as epinephrine and dipivefrin (act to increase outflow of aqueous humor through trabecular meshwork and possibly through uveoscleral outflow pathway, probably by a beta 2-agonist action); carbonic anhydrase inhibitors such as dorzolamide, brinzolamide, acetazolamide (lower secretion of aqueous humor by inhibiting carbonic anhydrase in the ciliary body); rho-kinase inhibitors (lower IOP by disrupting the actin cytoskeleton of the trabecular meshwork; vaptans (vasopressin-receptor antagonists); anecortave acetate and analogues; ethacrynic acid; cannabinoids; cholinergic agonists including direct acting cholinergic agonists (miotic agents, parasympathomimetics) such as carbachol, pilocarpine hydrochloride; pilocarpine nitrate, and pilocarpine (acts by contraction of the ciliary muscle, tightening the trabecular meshwork and allowing increased outflow of the aqueous humor); cholinesterase inhibitors such as demecarium, echothiophate and physostigmine; glutamate antagonists; calcium channel blockers including memantine, amantadine, rimantadine, nitroglycerin, dextrorphan, dextromethorphan, dihydropyridines, verapamil, emopamil, benzothiazepines, bepridil, diphenylbutylpiperidines, diphenylpiperazines, fluspirilene, eliprodil, ifenprodil, tibalosine, flunarizine, nicardipine, nifedipine, nimodipine, barnidipine, verapamil, lidoflazine, prenylamine lactate and amiloride; prostamides such as bimatoprost, or pharmaceutically acceptable salts or prodrugs thereof; and prostaglandins including travoprost, cloprostenol, fluprostenol, 13,14-dihydro-cloprostenol, isopropyl unoprostone, and latanoprost; AR-I 02 (a prostaglandin FP agonist available from Aerie Pharmaceuticals, Inc.); AL-3789 (anecortave acetate, an angiostatic steroid available from Alcon); AL-6221 (travoprost travatan a prostaglandin FP agonist; PF-03187207 (a nitric oxide donating prostaglandin available from by Pfizer) PF-04217329 (also available from Pfizer); INS1 15644 (a latrunculin B compound available from Inspire Pharmaceuticals), and; INS1 17548 (Rho-kinase inhibitor also available from inspire Pharmaceuticals).

Combinations of ocular anti-hypertensives, such as a beta blocker and a prostaglandin/prostamide analogue, can also be used in the delivery systems described herein. These include bimatoprost/timolol, travoprost/timolol, latanoprost/timolol, brimonidine/timolol, and dorzolamide/timolol. In combination with an IOP lowering therapeutic agent, an agent that confers neuroprotection can also be placed in the delivery system and includes memantine and serotonergics [e.g., 5-$HT_2$ agonists, such as but no limited to, S-(+)-I-(2-aminopropyl)-indazole-6-01)].

Other therapeutic agents outside of the class of ocular hypotensive agents can be used with the intracameral implants to treat a variety of ocular conditions. For example, anti-VEGF and other anti-angiogenesis compounds can be used to treat neovascular glaucoma. Another example is the use of corticosteroids or calcineurin inhibitors that can be used to treat diseases such as uveitis and corneal transplant rejection. These implants can also be placed in the subconjunctival space and in the vitreous.

Additionally, described herein are novel methods for making implants. The therapeutic agent of the present implants is preferably from about 1% to about 90% by weight of the implant. More preferably, the therapeutic agent is from about 5% to about 30% by weight of the implant. In a preferred embodiment, the therapeutic agent is an anti-hypertensive agent and comprises about 15% by weight of the implant (e.g., 5%-30 weight %). In another embodiment, the anti-hypertensive agent comprises about 20% or about 30% by weight of the implant.

In addition to the therapeutic agent, the implants described herein can include or may be provided in compositions that include effective amounts of buffering agents, preservatives and the like. Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents can be present in amounts sufficient to maintain a pH of the system of between about 2 to about 9 and more preferably about 4 to about 8. As such the buffering agent may be as much as about 5% by weight of the total implant. Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These agents may be present in amounts of from about 0.001% to about 5% by weight and preferably about 0.01% to about 2% by weight of the implant.

In one embodiment, a preservative such as benzalkonium chloride is provided in the implant. In another embodiment, the implant can include both benzalkonium chloride and bimatoprost. In yet another embodiment, the bimatoprost is replaced with latanoprost.

Various techniques may be employed to produce the implants described herein. Useful techniques include, but are not necessarily limited to, self-emulsification methods, super critical fluid methods, solvent evaporation methods, phase separation methods, spray drying methods, grinding methods, interfacial methods, molding methods, injection molding methods, combinations thereof and the like.

In one embodiment, the methods for making the implants involve dissolving the appropriate polymers and therapeutic agents in a solvent. Solvent selection will depend on the polymers and therapeutic agents chosen. For the implants described herein, including a therapeutic agent such as latanoprost, dichloromethane (DCM) is an appropriate solvent. Once the polymers and therapeutic agent(s) have been dissolved, the resulting mixture is cast into a die of an appropriate shape.

Then, once cast, the solvent used to dissolve the polymers and therapeutic agent(s) is evaporated at a temperature between about 20° C. and about 30° C., preferably about 25° C. The polymer can be dried at room temperature or even in a vacuum. For example, the cast polymers including therapeutic agents can be dried by evaporation in a vacuum.

The dissolving and casting steps form the implants because dissolving the polymers and therapeutic agents allows the system to naturally partition and form into its most natural configuration based on properties such as polymer viscosity and hence molecular weight, polymer hydrophobicity/hydrophilicity, therapeutic agent molecular weight, therapeutic agent hydrophobicity/hydrophilicity and the like.

Once the cast polymers are dried, they can be processed into an implant using any method known in the art to do so. In an example embodiment, the dried casted polymer can be cut into small pieces and extruded into rounded or squared rod shaped structures at a temperature between about 50° C. and about 120° C., preferably about 90° C. In other example embodiments, the films can simply be cast without extrusion.

Other methods involve extrusion of dry polymer powders and dry or liquid therapeutic agents. The implants are extruded and formed into a random orientation depending on the dry powder mix itself and not based on physical properties of the components. Prostaglandins such as latanoprost are very difficult to incorporate into hot-melt extruded implants because they generally exude the prostaglandin when heated. Therefore, the extrusion temperature is kept as low as possible to avoid loss and degradation of the prostaglandin. This can be accomplished by using a select combination of appropriate molecular weight polymers and a plasticizer like (polyethyleneglycol) PEG that are compatible with the prostaglandin. The prostaglandin and PEG plasticize the polymers to a degree that allows the mixture to be extruded at a temperature where the prostaglandin is not degraded or lost.

The therapeutic agent containing implants disclosed herein can be used to treat other ocular conditions in addition to glaucoma and/or increased IOP, such as the following: maculopathies/retinal degeneration: macular degeneration, including age related macular degeneration (ARMD), such as non-exudative age related macular degeneration and exudative age related macular degeneration, choroidal neovascularization, retinopathy, including diabetic retinopathy, acute and chronic macular neuroretinopathy, central serous chorioretinopathy, and macular edema, including cystoid macular edema, and diabetic macular edema. Uveitis/retinitis/choroiditis: acute multifocal placoid pigment epitheliopathy, Behcet's disease, birdshot retinochoroidopathy, infectious (syphilis, lyme, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpiginous choroiditis, subretinal fibrosis, uveitis syndrome, and Vogt-Koyanagi-Harada syndrome. Vascular diseases/exudative diseases: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasia, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, Eales disease. Traumatic/surgical: sympathetic ophthalmia, uveitic retinal disease, retinal detachment, trauma, laser, PDT, photocoagulation, hypoperfusion during surgery, radiation retinopathy, bone marrow transplant retinopathy. Proliferative disorders: proliferative vitreal retinopathy and epiretinal membranes, proliferative diabetic retinopathy. Infectious disorders: ocular histoplasmosis, ocular toxocariasis, presumed ocular histoplasmosis syndrome (PONS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis. Genetic disorders: retinitis pigmentosa, systemic disorders with associated retinal dystrophies, congenital stationary night blindness, cone dystrophies, Stargardt's disease and fundus flavimaculatus, Bests disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum. Retinal tears/holes: retinal detachment, macular hole, giant retinal tear. Tumors: retinal disease associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors. Miscellaneous: punctate inner choroidopathy, acute posterior multifocal placoid pigment epitheliopathy, myopic retinal degeneration, acute retinal pigment epithelitis and the like.

In one example embodiment, an implant comprising both PLA, PEG and PLGA and including an anti-hypertensive agent is used because implants of such a composition result in significantly less inflammatory (e.g. less corneal hyperemia) upon intracameral or anterior vitreal administration. Another embodiment can comprise a therapeutic agent delivery system with a plurality of anti-hypertensive agents contained in different segments of the same implant. For example, one segment of an implant can contain a muscarinic anti-hypertensive agent, a second segment of the implant can contain a anti-hypertensive prostaglandin and third segment of the implant can contain an anti-hypertensive beta blocker. Such an implant can be injected to enhance aqueous outflow through the trabecular meshwork, to enhance uveoscleral flow and to reduce aqueous humor production. Multiple hypotensive agents with different mechanisms of action can be more effective at lowering IOP than monotherapy, that is use of a single type of an anti-hypertensive agent. A multiple segmented implant has the advantage of permitting lower doses of each separate therapeutic agent used than the dose necessary with monotherapy, thereby reducing the side effects of each therapeutic agent used.

In one embodiment, when using a multiple segmented implant, each segment is preferably has a length no greater than about 2 mm. Preferably, the total number of segments administered through a 22 G to 25 G diameter needle bore is about four. With a 27 G diameter needle total segments length within the needle bore or lumen can be up to about 12 mm.

The fluid uptake action of the TM can be exploited to keep implants that have an appropriate geometry from floating around the anterior chamber causing visual obscuration. Gravity brings these implants down to about the 6 o'clock position, for example from about 20 degrees plus or minus, and the implants are stable (immobile) in this position. Implants that can be intraocularly administered by a 22 G to 30 G diameter needle with lengths totaling no more than about 6 to 8 mm are most preferred to take advantage of the TM fluid uptake mechanism with resulting intraocular implant immobility and no visual obscuration. Thus, despite being firmly in the 6 o'clock position in the anterior chamber due to TM fluid uptake effect, the implants can have release rates that exceed the TM clearance rate and this allows therapeutic agent(s) released by the implants to rapidly fill the anterior chamber and distribute well into the target tissues along a 360 degrees distribution pattern. Examination of implants in the angle of the anterior chamber with gonioscopy have shown that the there is no encapsulation of nor inflammatory tissue in the vicinity of the implants.

Delivery of therapeutic agents to the front of the eye (anterior chamber) can both lower intraocular pressure (IOP) and evade aggressive clearance of the transscleral barriers. Intracameral injections (i.e. direct injection into the anterior chamber) of implants as described herein and anterior vitreous injections of the same through the pars plana effectively avoid the transscleral barriers and improve the efficacy of the ocular anti-hypertensive compounds. Importantly, the present implants required development of new sustained released therapeutic agent delivery systems with particular physical features and required therapeutic efficacy because of the unique anatomy and physiology of the anterior chamber.

In one example embodiment, bimatoprost can be used in the implants described herein. Bimatoprost may improve aqueous outflow through the trabecular meshwork (TM) mediated through a prostamide receptor. In the human eye, the main outflow route is the trabecular or conventional outflow pathway. This tissue contains three differentiated layers. From the inner to the outermost part, the layer of tissue closest to the anterior chamber is the uveal meshwork, formed by prolongations of connective tissue arising from the iris and ciliary body stromas and covered by endothelial cells. This layer does not offer much resistance to aqueous humor outflow because intercellular spaces are large. The next layer, known as the corneoscleral meshwork, is characterized by the presence of lamellae covered by endothelium-like cells on a basal membrane. The lamellae are formed by glycoproteins, collagen, hyaluronic acid, and elastic fibers. The higher organization of the corneoscleral meshwork, in relation to the uveal meshwork, as well as their narrower intercellular spaces, are responsible for the increase in flow resistance. The third layer, which is in direct contact with the inner wall of endothelial cells from Schlemm's canal, is the juxtacanalicular meshwork. It is formed by cells embedded in a dense extracellular matrix, and the majority of the tissue resistance to aqueous flow is postulated to be in this layer, due to its narrow intercellular spaces. The layer of endothelial cells from Schlemm's canal has expandable pores that transfer the aqueous into the canal and accounts for approximately 10% of the total resistance. It is thought that aqueous humor crosses the inner wall endothelium of Schlemm's canal by two different mechanisms: a paracellular route through the junctions formed between the endothelial cells and a transcellular pathway through intracellular expandable pores of the same cells. Once there is entry into Schlemm's canal (FIG. 2), the aqueous drains directly into the collector ducts and aqueous veins that anastomose with the episcleral and conjunctival plexi of vessels. Aqueous humor outflow via the trabecular pathway is IOP dependent, usually measured as outflow facility, and expressed in microliters per minute per millimeter of mercury.

The episcleral venous pressure controls outflow through the collector channels and is one factor that contributes to the intraocular pressure. Increases in the episcleral venous pressure such as seen with carotid-cavernous sinus fistulas, orbital varices, and Sturge-Weber Syndrome, can lead to difficult to manage glaucoma. Reducing episcleral venous pressure in disease states, such as treating carotid-cavernous sinus fistulas, can normalize the episcleral venous pressure and reduce the intraocular pressure. Targeting the outflow channels and vessels to reduce the episcleral venous pressure with pharmacotherapy may reduce the IOP.

EXAMPLE 1

A series of three experiments were performed comparing the fluctuations of IOP over time in groups of animals treated with either bimatoprost eye drops or an intracameral sustained release bimatoprost implant as described herein. IOPs were recorded over time and the mean of the IOPs for each animal was calculated after dosing. The standard deviation (SD) of the mean was used to compare the variability of IOP control for each animal, and the average of all the SD means was calculated. A lower number for example, would correspond to less IOP fluctuation. This final SD value was calculated for all animals in the topical dosed group and also calculated for all animals receiving an intracameral implant, and the values were compared to determine if the intracameral implants were more effective at reducing IOP fluctuation.

Experiment 1:

Six normal beagle dogs had one drop bimatoprost 0.03% ophthalmic solution (LUMIGAN®) instilled in the left eye daily. Recordings of IOP were made with a pneumatonometer at about 10 am. Table 1 displays IOP recordings in mmHG at weekly intervals for 1 month in 6 dogs taking daily bimatoprost eye drops. The average of the mean of the SD for each animal is 1.38 mm Hg.

TABLE 1

Bimatoprost 0.03% Ophthalmic Drops: IOP Results

|  | Dog A | Dog B | Dog C | Dog D | Dog E | Dog F |
|---|---|---|---|---|---|---|
| Baseline IOP (mmHG) | 15.7 | 20.2 | 16.5 | 20.7 | 12.7 | 20.7 |
| Day 8 | 8.3 | 8.0 | 9.7 | 10.0 | 10.0 | 7.5 |
| Day 15 | 7.2 | 6.2 | 8.8 | 9.0 | 6.8 | 10.3 |
| Day 22 | 8.5 | 7.8 | 12.8 | 9.2 | 7.5 | 14.5 |
| Day 29 | 9.0 | 7.7 | 11.7 | 9.3 | 9.5 | 11.3 |
| Mean | 8.3 | 7.4 | 10.8 | 9.4 | 8.5 | 10.9 |
| SD | 0.76 | 0.83 | 1.83 | 0.43 | 1.54 | 2.89 |

Figure 4:
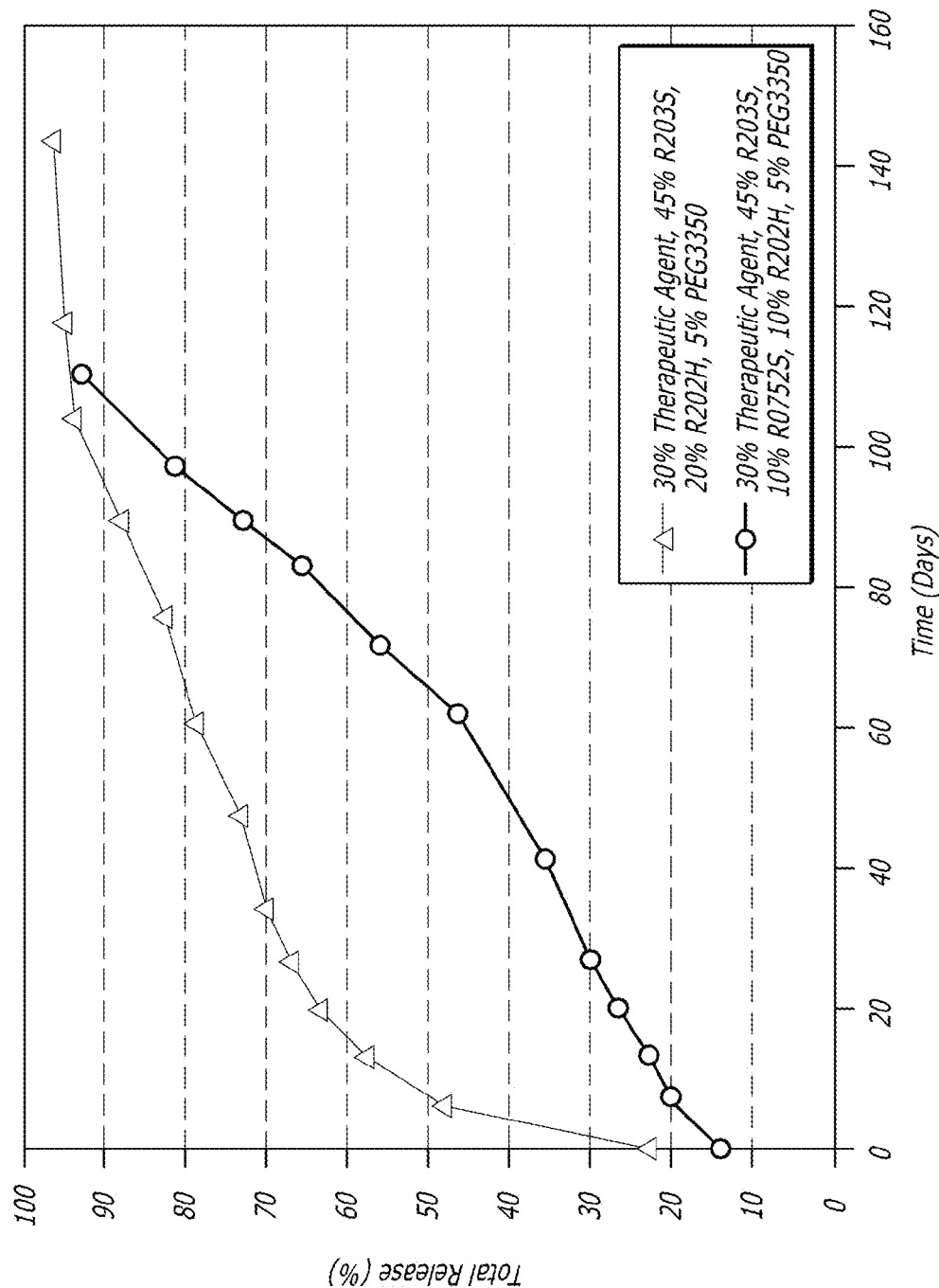
FIG. 4 graphically illustrates a release profile of implants of the present description.

Experiment 2:

A bimatoprost implant with a formulation containing 30% therapeutic agent, 45% R203S, 20% R202H and 5% PEG 3350 was manufactured with a total implant weight of 900 ug (drug load 270 ug). The in vitro release rates of this implant are graphically illustrated in FIG. 4. This implant released about 70% over first 30 days. An implant with a 270 ug drug load would release 189 ug over first 30 days or 6.3 ug per day. The remainder of the implant (81 ug) is released over the next four months (e.g. 675 ng per day).

Normal beagle dogs were given general anesthesia and a 3 mm wide keratome blade was used to enter the anterior chamber of the right eyes. A bimatoprost implant was placed in the anterior chamber and it settled out in the inferior angle within 24 hours. The IOP results are shown in Table 2. The average of the mean of the SD for each animal is 0.57 mm Hg with Dog #4 having a first month mean SD of 0.

TABLE 2

Intracameral Bimatoprost Implant: IOP Results

|  | Dog #1 120 ug | Dog #2 120 ug | Dog #3 120 ug | Dog #4 270 ug |
|---|---|---|---|---|
| Baseline IOP (mmHG) | 17.0 | 16.5 | 22.5 | 25.0 |
| Day 7 | 11.5 | 9.0 | 14.0 | 9.0 |
| Day 14 | 10.5 | 9.0 | 14.5 | n/a |
| Day 21 | 11.5 | 11.0 | 13.5 | n/a |
| Day 28 | 11.0 | 11.0 | 13.0 | 9.0 |
| Mean | 11.1 | 10.0 | 13.8 | 9.0 |
| SD | 0.48 | 1.15 | 0.65 | 0 |

Figure 5:
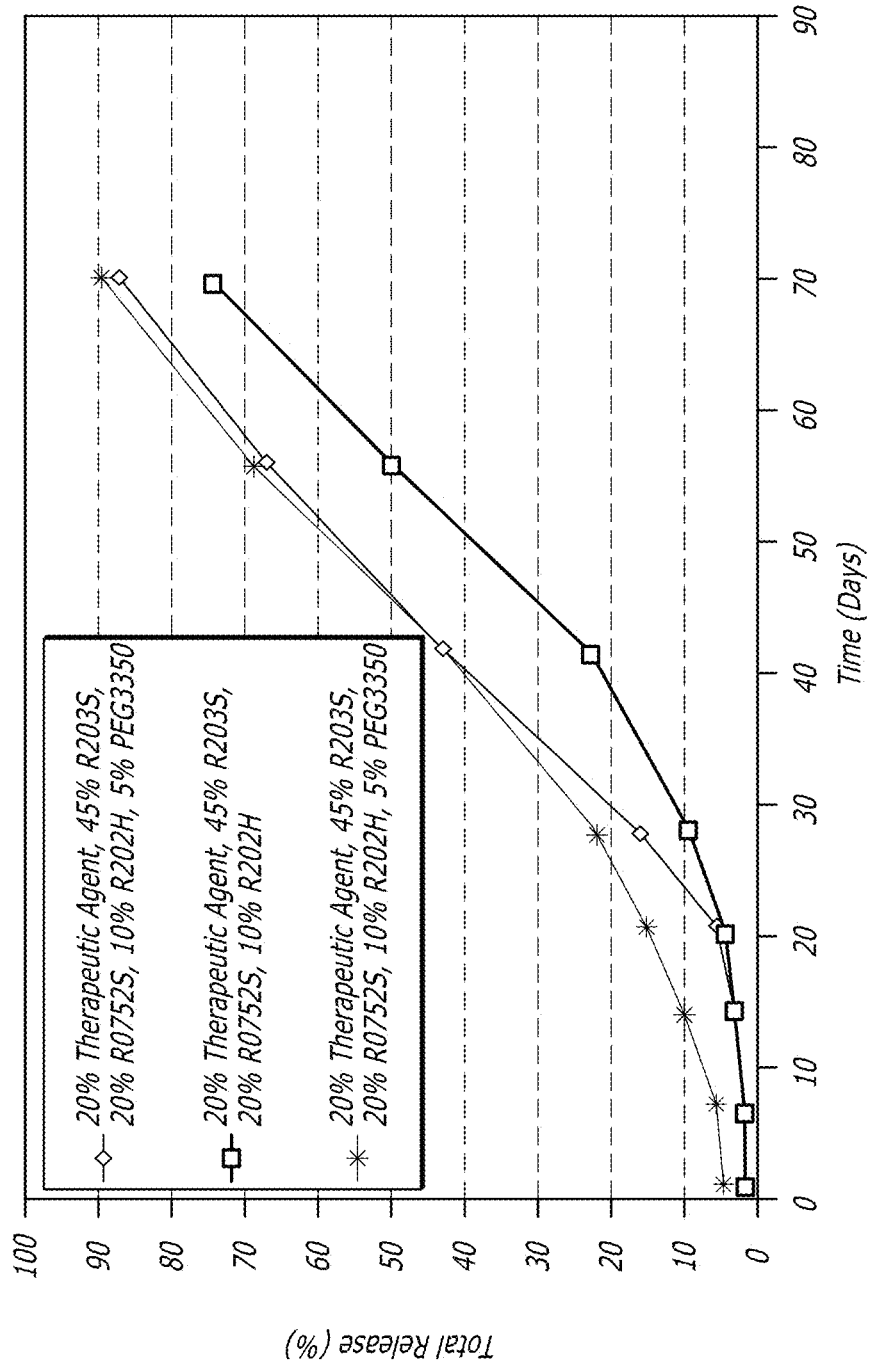
FIG. 5 graphically illustrates a release profile of implants of the present description.

Experiment 3:

An additional bimatoprost implant formulation with 20% therapeutic agent, 45% R203S, 10% R202H, 20% RG752S and 5% PEG 3350 formulation was manufactured with a total implant weight of about 300 ug (drug load of about 60 ug). Implant weights are shown in Table 3, each animal received two implants. The in vitro release rates of this implant are shown in FIG. 5. Table 3 shows implant weights and therapeutic agent loads used in the dogs for Experiment 3. Each animal received 2 intracameral implants to 1 eye. The implants release about 15% of the drug load over the first month. An implant with a 60 ug drug load would release 9 ug over the first 30 days or 300 ng per day, thereafter. In other words, the implant releases about 50 ug over 60 days or about 700 ng/day.

TABLE 3

Implant weights

| Dog ID | Implant Weight (mg) | Total Therapeutic Agent Dose (20% load, ug) |
|---|---|---|
| Dog #1 | 0.302 | 126.6 |
|  | 0.331 |  |
| Dog #2 | 0.298 | 125.4 |
|  | 0.329 |  |
| Dog #3 | 0.0306 | 126.6 |
|  | 0.327 |  |

Figure 6:
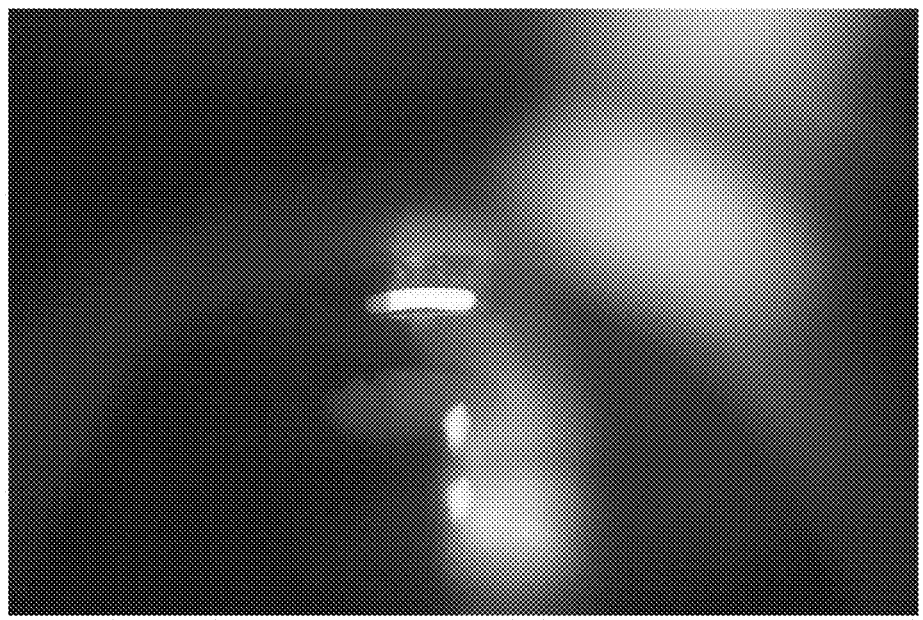
FIG. 6 illustrates the placement of an implant according the present description.

Implants were loaded in customized applicators with a 25 G UTW needles. Under general anesthesia, normal beagle dogs had the implant inserted in the right anterior chamber through clear cornea and the wound was self-sealing. Each animal (n=3) received two implants in the right eye. The implant demonstrated no inflammation clinically and a representative photograph of an implant in the anterior chamber is seen in FIG. 6. The IOP results and the SD of the mean over the first month are shown in Table 2. The average of the mean of the SD's in Table 2 of the four dogs (total) from experiments 2 and 3 treated with bimatoprost implants was 0.57 mmHg.

The variability in the IOP of the dogs in Experiment 1 dosed with bimatoprost eye drops as measured by the final SD value was 1.38 mmHg. In contrast, the final SD value with sustained-release bimatoprost implants was 0.57 mmHg. There was approximately a three-fold reduction in the final SD value demonstrating that sustained-release bimatoprost implant described herein is superior to bolus dosing with topical bimatoprost to reduce IOP fluctuations over time.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A method for treating an ocular condition comprising the steps of: providing at least two biodegradable sustained release implants containing at least one therapeutic agent; implanting the at least two biodegradable sustained release implants into the anterior chamber of an eye; and treating the ocular condition, wherein the at least two biodegradable sustained release implants release about 100 ng per day of the at least one bioactive agent for a period greater than about 1 month.

2. The method according to claim 1 wherein the ocular condition is glaucoma.

3. The method according to claim 1 wherein the ocular condition is elevated intraocular pressure.

4. The method according to claim 1 wherein the sustained release implant releases about 70% of the at least one therapeutic agent over the first month.

5. The method according to claim 1, wherein the at least one therapeutic agent is selected from the group consisting of latanoprost, bimatoprost and travoprost and their salts, esters and prodrugs.

6. The method according to claim 1 wherein the at least two biodegradable sustained release implants comprise about 30% therapeutic agent.

7. The method according to claim 1 wherein the at least two biodegradable sustained release implants comprise about 5% to about 70% poly(D,L-lactide).

8. The method according to claim 1 wherein the at least two biodegradable sustained release implants comprise about 5% to about 40% poly(D,L-lactide-co-glycolide).

9. The method according to claim 1 wherein the at least two biodegradable sustained release implants comprise about 5% to about 40% polyethylene glycol.

10. The method according to claim 1 wherein the at least two biodegradable sustained release implants comprise about 30% therapeutic agent, 65% poly(D,L-lactide), and 5% polyethylene glycol.

11. The method according to claim 1 wherein the at least two biodegradable sustained release implants comprise about 30% therapeutic agent, 65% poly(D,L-lactide), and 5% polyethylene glycol.

12. The method according to claim 1 wherein the at least two biodegradable sustained release implants comprise about 20% therapeutic agent, 55% poly(D,L-lactide), 10% poly(D,L-lactide-co-glycolide), and 5% polyethylene glycol.

13. The method according to claim 1 wherein the implanting step is accomplished using an applicator.

14. The method according to claim 1 wherein the at least two biodegradable sustained release implants are settled out in the inferior angle within 24 hours of implanting within the anterior chamber.

* * * * *

UNITED STATES PATENT AND TRADEMARK OFFICE
CERTIFICATE OF CORRECTION

PATENT NO. : 9,504,696 B2
APPLICATION NO. : 14/746438
DATED : November 29, 2016
INVENTOR(S) : Michael R. Robinson et al.

It is certified that error appears in the above-identified patent and that said Letters Patent is hereby corrected as shown below:

On the Title Page

On the page 2, in Column 2, under "Other Publications", Line 33, after "filed" insert -- on --.

In the Specification

In Column 4, Line 67, delete "lop" and insert -- IOP --, therefor.

In Column 10, Line 53, delete "CI" and insert -- Cl --, therefor.

In Column 12, Line 40, delete "no" and insert -- not --, therefor.

Signed and Sealed this
Twenty-first Day of February, 2017

Michelle K. Lee
*Director of the United States Patent and Trademark Office*